United States Patent [19]

Punja

[11] 4,198,347

[45] Apr. 15, 1980

[54] 2(2,2-DICHLOROVINYL)-3,3-DIMETHYL-CYCLOPROPANE CARBOXYLATES

[75] Inventor: Nazim Punja, Wokingham, England

[73] Assignee: Imperial Chemical Industries Limited, London, England

[21] Appl. No.: 925,239

[22] Filed: Jul. 17, 1978

Related U.S. Application Data

[62] Division of Ser. No. 684,956, May 10, 1976, abandoned.

[30] Foreign Application Priority Data

May 16, 1975 [GB] United Kingdom ............... 20884/75
May 16, 1975 [GB] United Kingdom ............... 20885/75
May 16, 1975 [GB] United Kingdom ............... 20893/75

[51] Int. Cl.$^2$ .................... C07C 69/74; C07C 121/48
[52] U.S. Cl. ................. 260/464; 260/465.4; 560/124; 562/506
[58] Field of Search ................. 260/464; 560/124

[56] References Cited

U.S. PATENT DOCUMENTS 3,658,879  4/1972  Julia ................... 260/464
4,000,180  12/1976 Punja .................. 560/124

FOREIGN PATENT DOCUMENTS 832278  2/1976  Belgium .
833278  3/1976  Belgium .

OTHER PUBLICATIONS

Kondo, "Japan Chemical Ass., The 31st Autumn Annual Meeting, Abstracts", vol I. 4A04, p. 58 (1974).
Farkas et al., Collection Czechoslov. Chem. Commun., vol. 24, pp. 2230–2236 (1959).
Elliott et al., Nature, vol. 244, pp. 456–457 (1973).

*Primary Examiner*—Dolph H. Torrence
*Attorney, Agent, or Firm*—Cushman, Darby & Cushman

[57] ABSTRACT

Preparation of ethyl 2(2,2-dichlorovinyl)-3,3-dimethyl-1-ethoxycarbonylcyclopropane carboxylate and ethyl 1-cyano-2(2,2-dichlorovinyl)-3,3-dimethyl-cyclopropanecarboxylate as intermediates.

2 Claims, No Drawings

2(2,2-DICHLOROVINYL)-3,3-DIMETHYL-CYCLOPROPANE CARBOXYLATES

This is a division of application Ser. No. 684,956 filed May 10, 1976 and now abandoned.

The present invention relates to a process for the preparation of valuable chemical intermediates.

2(2,2-Dichlorovinyl)-3,3-dimethylcyclopropane carboxylic acid is an important intermediate in the production of insecticides, including for example, 3-phenoxybenzyl 2(2,2-dichlorovinyl)-3,3-dimethylcyclopropane carboxylate. The preparation of 2(2,2-dichlorovinyl)-3,3-dimethylcyclopropane carboxylic acid has been described by Farkas et al (Collection Czechoslov, Chem. Commun., (1959), 24, pp 2230–2236) by the reaction of ethyl diazoacetate with 1,1-dichloro-4-methyl-1,3-pentadiene followed by hydrolysis of the resultant ethyl ester. This process is not suitable for large scale preparation of the acid because of the difficulties of working with ethyl diazoacetate, which is a substance which can explosively decompose unless the conditions are rigourously controlled, and which is believed to be a potent carcinogen.

We have now discovered that the above acid may be prepared by a process which does not involve the use of diazoacetate.

Accordingly the present invention provides a process for the preparation of a compound of formula:

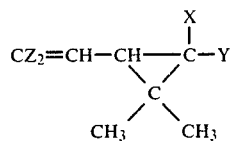

Wherein X and Y are independently selected from cyano and alkoxycarbonyl containing from 1 to 4 carbon atoms in the alkoxy moiety, and Z is chlorine or bromine, which comprises (a) the step of treating a compound of formula:

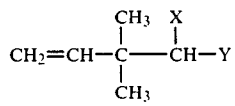

with a tetrahalomethane of formula $CZ_2QR$, where Q and R are independently selected from chlorine and bromine provided that Q is always bromine when either of Z and R are bromine, in the presence of a free radical catalyst, and (b) the step of treating the compound of formula:

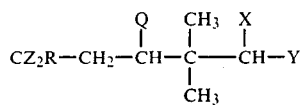

obtained in step (a) with at least two molar equivalent of a base.

Although any tetrahalomethane of the formula $CZ_2QR$ wherein Z, Q and R are as defined above may be used, those which are particularly preferred are those which lead to compounds wherein Z is chlorine, for example carbon tetrachloride and bromotrichloromethane.

The reaction outlined in step (a) is free radical in nature and is carried out in the presence of a free-radical catalyst, which term includes a free-radical initiator such as irradiation with a suitable, e.g. Ultra violet, light source, as well as conventional chemical free radical catalysts such as for example benzoyl peroxide and azobisisobutyronitrile.

The reaction may conveniently be carried out using an excess of the compound of formula $CZ_2QR$ as a diluent, at temperatures in the range 50° C. to 100° C., preferably 80°–90° C., at periods from 1 to 20 hours.

The product of the reaction of step (a) is a compound of formula:

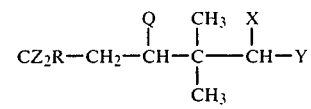

wherein X, Y, Z, Q and R are as defined above. Such compounds have not been previously described and are part of the present invention. Examples of such compounds are ethyl 4-bromo-3,3-dimethyl-1-ethoxycarbonyl-6,6,6-trichlorohexanoate, ethyl 3,3-dimethyl-1-ethoxycarbonyl-4,6,6,6-tetrachlorohexanoate, ethyl 4-bromo-1-cyano-3,3-dimethyl-6,6,6-trichlorohexanoate and ethyl 1-cyano-3,3-dimethyl-4,6,6,6-tetrachlorohexanoate.

The compounds of formula:

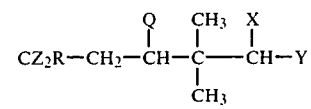

are subjected in step (b) of the process to treatment with at least two moles of a base. This part of the process involves two separate stages, cyclisation and β-elimination of hydrogen halide, but is is not clear in what order these two stages proceed, or if they proceed simultaneously. The product of the process is a cyclopropane derivative of formula:

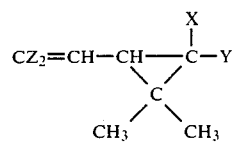

Suitable bases for carrying out the process include tertiary amines, for example pyridine, triethylamine, diethylaniline, N-methyl piperidine, and also alkali metal alkoxides, for example sodium methoxide, sodium ethoxide, and potassium t-butoxide. The step is conveniently carried out in a diluent or solvent for the reactant and the base. A particularly convenient manner of conducting this step is to heat a solution of the reactant in an alcohol corresponding to the alkali metal alkoxide being used as base for a period of from 1 to 20 hours.

The products of the process are as stated above compounds of formula:

$$CZ_2=CH-CH\underset{\underset{CH_3}{\diagdown}\underset{CH_3}{\diagup}C}{\overset{X}{-}}C-Y$$

where X, Y and Z have any of the meanings given herein.

They are also novel compounds and as such form part of the present invention. Examples of particular compounds of this type include ethyl 2-(2,2-dichlorovinyl)-3,3-dimethyl-1-ethoxycarbonylcyclopropane carboxylate, and ethyl 1-cyano-2-(2,2-dichlorovinyl)-3,3-dimethylcyclopropane carboxylate.

The compounds of formula:

$$CH_2=CH-\underset{\underset{CH_3}{|}}{\overset{\overset{CH_3}{|}}{C}}-\overset{X}{\underset{}{C}}H-Y$$

wherein X and Y have any of the meanings given herein may be prepared by reduction of the corresponding acetylene derivatives of formula:

$$CH\equiv C-\underset{\underset{CH_3}{|}}{\overset{\overset{CH_3}{|}}{C}}-\overset{X}{\underset{}{C}}H-Y$$

This reduction is most conveniently carried out by hydrogenation of the acetylene derivative under pressure in the presence of a partially poisoned palladium catalyst, for example palladium deposited on charcoal in the presence of quinoline. This type of catalyst system allows reduction of the acetylene derivative to the corresponding alkenyl derivative, but does not permit further reduction to the fully saturated alkyl derivative.

In a further aspect the invention provides a process for preparing a compound of the formula:

$$CZ_2=CH-CH\underset{\underset{CH_3}{\diagdown}\underset{CH_3}{\diagup}C}{\overset{X}{-}}C-Y$$

as defined hereinabove in which the compound of formula:

$$CH_2=CH-\underset{\underset{CH_3}{|}}{\overset{\overset{CH_3}{|}}{C}}-\overset{X}{\underset{}{C}}H-Y$$

is obtained by the hydrogenation under pressure of a compound of formula:

$$CH\equiv C-\underset{\underset{CH_3}{|}}{\overset{\overset{CH_3}{|}}{C}}-\overset{X}{\underset{}{C}}H-Y$$

in the presence of a partially poisoned palladium catalyst, wherein X and Y are as defined hereinabove.

In a yet further aspect of the invention the compounds of formula:

$$CZ_2=CH-CH\underset{\underset{CH_3}{\diagdown}\underset{CH_3}{\diagup}C}{\overset{X}{-}}C-Y$$

wherein X is selected from cyano and alkoxycarbonyl containing from 1 to 4 carbon atoms in the alkoxy moiety and Y is alkoxycarbonyl containing from 1 to 4 carbon atoms in the alkoxy moiety may be converted to the corresponding compounds of formula:

$$CZ_2=CH-CH\underset{\underset{CH_3}{\diagdown}\underset{CH_3}{\diagup}C}{-}CH-X$$

by the extra step of heating in a polar aprotic solvent having a boiling point greater than 150° C. in the presence of an alkali metal halide or cyanide. Preferred alkali metal halides are potassium iodide and sodium chloride. A suitable alkali metal cyanide is sodium cyanide. The reaction is conveniently carried out in the presence of at least two molar equivalents of water with respect to the cyclopropane derivative.

In an alternative extra step the compound of formula:

$$CZ_2=CH-CH\underset{\underset{CH_3}{\diagdown}\underset{CH_3}{\diagup}C}{\overset{X}{-}}C-Y$$

is subjected to the processes of (i) saponification with an alkali metal hydroxide, (ii) acidification with a mineral acid, and (iii) decarboxylation through heating to yield a compound of formula:

$$CZ_2=CH-CH\underset{\underset{CH_3}{\diagdown}\underset{CH_3}{\diagup}C}{-}CH-CO_2H$$

The invention is illustrated by the following Examples.

EXAMPLE 1

This Example illustrates the preparation of ethyl 3,3-dimethyl-2-ethoxycarbonylpent-4-ynoate.

Diethyl malonate (34.8 g.) was added to a solution of sodium (5.0 g.) in ethanol (500 ml.) and the mixture stirred for a few minutes. 3,3-Dimethyl-1-bromoallene (32.0 g.) was then added dropwise at the ambient temperature after which the mixture was refluxed for 3 hours. The ethanolic solution obtained was poured into an excess of water and the mixture extracted with chloroform (3×200 ml.). The extracts were combined, dried with anhydrous sodium sulphate and evaporated and the residual oil distilled under reduced pressure to yield ethyl 3,3-dimethyl-2-ethoxycarbonylpent-4-ynoate, as an oil b.p. 56°–60°/0.1 mm.Hg.

EXAMPLE 2

This Example illustrates the preparation of ethyl 2-cyano1-3,3-dimethylpent-4-ynoate.

Ethyl cyanoacetate (77.0 g.) was slowly added at 40° C. to a stirred solution of sodium (15.7 g.) in ethanol (400 ml.) and 15 minutes after the addition was completed 1-bromo-3,3-dimethylallene (100 g.) was carefully added over about 30 minutes. The mixture was then heated at the reflux temperature for a period of 2.5 hours and then kept at the ambient temperature for a further 20 hours. The mixture was then poured into an excess of water and extracted with chloroform. The extract was washed with water, dried over anhydrous magnesium sulphate and concentrated by evaporation of the solvent. The residual oil was distilled and ethyl 2-cyano-3,3-dimethylpent-4-ynoate was obtained as a colourless oil (boiling point 75°–76° C./0.1 mm Hg.).

EXAMPLE 3

This Example illustrates the preparation of ethyl 3,3-diemethyl-2-ethoxycarbonylpent-4-enoate.

A solution of ethyl 3,3-dimethyl-2-ethoxycarbonylpent-4-ynoate (15.0 g.) in ethanol (300 ml.) is charged to a rocking autoclave fitted with a hydrogen inlet, and quinoline (3.0 ml.) and 3% palladium on charcoal (0.5 g. of a 50% aqueous paste) added. Hydrogen is passed into the autoclave which is maintained at a temperature of 35° to 40° C. and an internal pressure of 450 p.s.i.g. After a period of six hours the contents of the autoclave are filtered, the filtrate evaporated under reduced pressure to remove the ethanol, the residue dissolved in chloroform and the solution washed with dilute hydrochloric acid and with water and finally dried over anhyrous magnesium sulphate. Removal of the solvent by evaporation under reduced pressure and distillation of the residue yielded ethyl 3,3-dimethyl-1-ethoxycarbonylpent-4-enoate as a colourless oil identified by infrared and nuclear magnetic resonance spectroscopy.

EXAMPLE 4

By a procedure similar to that illustrated in Example 3 above ethyl 1-cyano-3,3-dimethylpent-4-ynoate is converted to ethyl 1-cyano-3,3-dimethylpent-4-enoate.

EXAMPLE 5

This Example illustrates the preparation of ethyl 4-bromo-3,3-dimethyl-1-ethoxycarbony-6,6,6-trichlorohexanoate.

A mixture of ethyl 3,3-dimethyl-2-ethoxycarbonylpent-4-enoate (8.0 g.), bromotrichloromethane (10.45 g.), carbon tetrachloride (120 ml.) and benzoyl peroxide (0.1 g.) was refluxed under a nitrogen atmosphere for a period of 20 hours, after which the mixture was cooled to the ambient temperature and washed with 10% w/v aqueous sodium bicarbonate solution and with water and then dried over anhydrous magnesium sulphate. The solvent was evaporated under reduced pressure and the residue was shown by infra-red, nuclear-magnatic resonance and mass spectroscopy to consist of ethyl 4-bromo-3,3-dimethyl-1-ethoxycarbonyl-6,6,6-trichlorohexanoate.

EXAMPLE 6

In a variation of the procedure of the previous Example a mixture of ethyl 3,3-dimethyl-2-ethoxycarbonylpent-4-enoate (99.5 g.), bromotrichloromethane (164 g.), carbon tetrachloride (650 ml.) and benzoyl peroxide (2.2 g.) was irradiated using a tungsten lamp whilst heating at the reflux temperature for a period of 18 hours. The product was obtained in 93% yield.

EXAMPLE 7

This Example illustrates the preparation of ethyl 4-bromo-3,3-dimethyl-2-ethoxycarbonyl-6,6,6-trichlorohexanoate.

A mixture of ethyl 3,3-dimethyl-2-ethoxycarbonylpent-4-enoate (6.5 g) and bromotrichloromethane (40 g.) is heated to 80°–90° C. for a period of 10 hours with periodic addition of benzoyl peroxide (total 0.6 g.), after which the excess bromotrichloromethane is removed by evaporation under reduced pressure and the residue distilled at the high vacuum pump to yield ethyl 4-bromo-3,3-dimethyl-2-ethoxycarbonyl-6,6,6-trichlorohexanoate.

EXAMPLE 8

This Example illustrates the preparation of ethyl 4-bromo-2,-cyano-3,3-dimethyl-6,6,6-trichlorohexanoate.

A mixture of ethyl 2-cyano-3,3-dimethylpent-4-enoate (0.4 g.) bromotrichloromethane (0.8 g.), carbon tetrachloride (2.0 ml.) and benzoyl peroxide (0.05 g.) was heated at the reflux temperature for 8 hours, and then allowed to cool to ambient temperature. Carbon tetrachloride (5.0 ml.) was added and the mixture washed with saturated sodium bicarbonate solution and with water. After drying the carbon tetrachloride solution over anhydrous magnesium sulphate the volatile portion was removed by evaporation under reduced pressure and the residue identified by infra-red spectroscopy as ethyl 4-bromo-2-cyano-3,3-dimethyl-6,6,6-trichlorohexanoate.

EXAMPLE 9

This Example illustrates the preparation of ethyl 2-(2,2-dichlorovinyl)-3,3-dimethyl-1-ethoxycarbonylcyclopropane carboxylate.

Ethyl 4-bromo-3,3-dimethyl-1-ethoxycarbonyl-6,6,6-trichlorohexanoate (184 g.) is slowly added at the ambient temperature to a stirred solution of sodium (18.5 g.) in ethanol (350 ml.). The mixture was refluxed for a period of 2 hours, after which it was poured into an excess of water and the mixture extracted with chloroform. The chloroform extracts were dried over anhydrous magnesium sulphate and concentrated by evaporation of the solvent. The residual oil was purified by distillation under reduced pressure and ethyl 2-(2,2-dichlorovinyl)-3,3-dimethyl-1-ethoxycarbonylpropane carboxylate was obtained as a colourless oil, boiling point 101°–103° C./0.1 mm Hg.

EXAMPLE 10

This Example illustrates the preparation of ethyl 2-(2,2-dichlorovinyl)-3,3-dimethylcyclopropane carboxylate.

A mixture of ethyl 2-(2,2-dichlorovinyl)-3,3-dimethyl-1-ethoxycarbonylcyclopropane carboxylate (5.0 g.), potassium iodide (2.5 g.), dry dimethylsulphoxide (12.0 ml.) and water (0.6 ml.) was heated at a temperature of 180° C. under a nitrogen atmosphere for a period of 9 hours, after which it was cooled to the ambient temperature, poured into water (250 ml.) and extracted with petroleum ether (boiling range 60° to 80° C., 3×50 ml.). The extracts were washed with water, dried over anhydrous magnesium sulphate and concentrated by evaporation of the solvent under reduced pressure. Examination of the residual oil by infra-red spectroscopy and gas-liquid chromatography indicated that ethyl 2-(2,2-dichlorovinyl)-3,3-dimethylcyclopropane carboxylate had formed in about 70% yield, and consisted of about 60% of the cis-isomer and 40% of the trans-isomer.

EXAMPLE 11

This Example illustrates the preparation of ethyl 2-(2,2-dichlorovinyl)-3,3-dimethylcyclopropane carboxylate.

A mixture of ethyl 2-(2,2-dichlorovinyl)-3,3-dimethyl-1-ethoxycarbonylcyclopropane carboxylate (5.0 g.), sodium chloride (0.95 g.), and 'wet' dimethylsulphoxide (6.0 ml.) was heated at a temperature of 175° to 180° C. under a nitrogen atmosphere for a period of 6 hours, after which it was cooled to the ambient temperature poured into water and extracted with petroleum ether (boiling range 60° to 80° C.). The extracts were dried over anhydrous magnesium sulphate and concentrated by evaporation of the solvent to yield a residue comprising about 60% of the cis-isomer and 40% of the trans-isomer of ethyl 2-(2,2-dichlorovinyl)-3,3-dimethylcyclopropane carboxylate in about 80% yield, identification of which was confirmed by comparison with authentic samples using infra-red spectroscopy and gas-liquid chromatography.

EXAMPLE 12

By a similar procedure to that illustrated in the previous Example ethyl 1-cyano-2-(2,2-dichlorovinyl)-3,3-dimethylcyclopropane carboxylate is converted to 1-cyano-2-(2,2-dichlorovinyl)-3,3-dimethylcyclopropane.

EXAMPLE 13

In a further experiment using the conditions of Example 10 except that sodium chloride was used in place of potassium iodide, ethyl 2-(2,2-dichlorovinyl)-3,3-dimethylcyclopropane carboxylate was obtained in 80% yield. The product consisted of about 55% of the cis-isomer and 45% of the trans-isomer.

EXAMPLE 14

This illustrates the preparation of ethyl 2-(2,2-dichlorovinyl)-3,3-dimethylcyclopropane carboxylate.

A mixture of ethyl 2(2,2-dichlorovinyl)-3,3-dimethyl-1-ethoxycarbonylcyclopropane carboxylate (1.0 g.), sodium cyanide (0.32 g.) and dry dimethylsulphoxide (10 ml.) was heated at a temperature of 160° C. for a period of 4 hours, after which it was cooled, poured into water, and the mixture extracted with diethyl ether. The ethereal extract was washed with water, dried over anhydrous magnesium sulphate and concentrated by evaporation of the ether. The residue was shown by infra-red spectroscopy and gas-liquid chromatography to comprise about 50% ethyl 2-(2,2-dichlorovinyl)-3,3-dimethylcyclopropane carboxylate together with about 50% of the starting material. The product consisting of about 50% of the cis-isomer and 50% of the trans-isomer.

EXAMPLE 15

This Example illustrates the preparation of 2,(2,2-dichlorovinyl)-3,3-dimethylcyclopropane carboxylic acid.

The mixture of ethyl 2-(2,2-dichlorovinyl)-3,3-dimethyl-1-ethoxycarbonylcyclopropanecarboxylate (1.5 g.) potassium hydroxide (2.0 g.) and ethanol (150 ml.) is refluxed for 2 hours, after which it is poured into water (500 ml.) and carefully acidified with concentrated hydrochloric acid. The white oily precipitate which is formed is collected by extraction with carbon tetrachloride, the extracts dried with anhydrous sodium sulphate, and the solvent evaporated under reduced pressure. The residual oil is heated under nitrogen to about 150°–160° C. for about 1.5 hours, and then cooled to form a crystalline mass. Recrystallisation from n-hexane yielded 2,2-dimethyl-3-(2,2-dichlorovinyl) cyclopropane carboxylic acid, m.p. 87°–90° C., believed to be principally the trans-isomer.

EXAMPLE 16

By a similar procedure to that illustrated in Example 9 ethyl 1-cyano-2-(2,2-dichlorovinyl)-3,3-dimethylcyclopropane carboxylate is obtained from ethyl-bromo-2-cyano-3,3-dimethyl-6,6,6-trichlorohexanoate.

I claim:
1. Ethyl 2(2,2-dichlorovinyl)-3,3-dimethyl-1-ethoxycarbonylcyclopropane carboxylate.
2. Ethyl 1-cyano-2(2,2-dichlorovinyl)-3,3-dimethylcyclopropanecarboxylate.

* * * * *